(12) United States Patent
Potharaju et al.

(10) Patent No.: US 11,273,281 B2
(45) Date of Patent: Mar. 15, 2022

(54) HUMIDIFIER HEATER BASE

(71) Applicant: Fisher & Paykel Healthcare Limited, Auckland (NZ)

(72) Inventors: Venkata Subbarao Potharaju, Auckland (NZ); Yi-Cheng Sun, Auckland (NZ); Dominique Richard D'Andrea, Auckland (NZ); Andrew Paul Maxwell Salmon, Auckland (NZ)

(73) Assignee: Fisher & Paykel Healthcare Limited, Auckland (NZ)

( * ) Notice: Subject to any disclaimer, the term of this patent is extended or adjusted under 35 U.S.C. 154(b) by 417 days.

(21) Appl. No.: 16/248,663

(22) Filed: Jan. 15, 2019

(65) Prior Publication Data

US 2019/0290877 A1    Sep. 26, 2019

Related U.S. Application Data

(63) Continuation of application No. 14/838,168, filed on Aug. 27, 2015, now Pat. No. 10,252,019, which is a
(Continued)

(51) Int. Cl.
*A61M 16/10*    (2006.01)
*A61M 16/16*    (2006.01)
*A61M 16/00*    (2006.01)

(52) U.S. Cl.
CPC ...... *A61M 16/109* (2014.02); *A61M 16/1045* (2013.01); *A61M 16/1075* (2013.01);
(Continued)

(58) Field of Classification Search
CPC ............ A61M 16/0066; A61M 16/024; A61M 16/1045; A61M 16/1075; A61M 16/109;
(Continued)

(56) References Cited

U.S. PATENT DOCUMENTS 3,659,604 A * 5/1972 Melville ........... A61M 16/1095
128/203.27
3,683,153 A    8/1972 Heyer
(Continued)

FOREIGN PATENT DOCUMENTS

AU    2005201817    5/2005
WO    WO 2002/066106    8/2002
(Continued)

OTHER PUBLICATIONS

Examination Report in corresponding German Patent Application No. 112010002249.6, dated Jun. 19, 2020, in 4 pages.
(Continued)

*Primary Examiner* — Annette Dixon
(74) *Attorney, Agent, or Firm* — Knobbe Martens Olson & Bear LLP

(57) ABSTRACT

A humidifier heater base assembly has a heater plate with a thermally conductive portion and a perimeter portion around a perimeter of the heater plate. A resilient member has an inner part attached to the perimeter portion and an outer part adapted to provide a resilient perimeter flange around at least part and preferably the whole of the perimeter portion. The resilient member fixes the heater base to the humidifier by the resilient perimeter flange such that the heater plate and the inner part can move relative to the humidifier in a direction substantially transverse to the general plane of the heater plate. At least a portion of the resilient perimeter flange remains stationary relative to the humidifier.

20 Claims, 10 Drawing Sheets

Related U.S. Application Data continuation of application No. 13/375,975, filed as application No. PCT/NZ2010/000103 on Jun. 3, 2010, now Pat. No. 9,174,017.

(60) Provisional application No. 61/184,379, filed on Jun. 5, 2009.

(52) U.S. Cl.
CPC ........ *A61M 16/1095* (2014.02); *A61M 16/16* (2013.01); *A61M 16/0066* (2013.01); *A61M 2207/10* (2013.01); *Y10T 29/49085* (2015.01)

(58) Field of Classification Search
CPC .............. A61M 16/1095; A61M 16/16; A61M 16/162; A61M 2205/3653; A61M 2207/10; A61M 2209/082; F24F 6/10; H05B 3/68; Y10S 261/65; Y10T 29/49085

See application file for complete search history.

(56) References Cited

U.S. PATENT DOCUMENTS

| | | | |
|---|---|---|---|
| 3,806,102 A | 4/1974 | Valenta et al. | |
| 3,841,798 A | 10/1974 | Rehfeld | |
| 4,028,444 A | 6/1977 | Brown et al. | |
| 4,083,439 A | 4/1978 | Chandler | |
| 4,098,853 A | 7/1978 | Brown et al. | |
| 4,201,737 A | 5/1980 | Carden | |
| 4,203,027 A * | 5/1980 | O'Hare | A61M 16/16 128/203.27 |
| 4,277,815 A | 7/1981 | Skroupa | |
| 4,331,827 A | 5/1982 | Keller | |
| 4,675,504 A | 6/1987 | Suhajda | |
| 4,676,237 A | 6/1987 | Wood et al. | |
| 4,849,285 A | 7/1989 | Dillon | |
| 4,859,383 A | 8/1989 | Dillon | |
| 5,015,427 A | 5/1991 | Sosnow | |
| 5,294,374 A | 3/1994 | Martinez et al. | |
| 5,558,084 A | 9/1996 | Daniell et al. | |
| 6,435,180 B1 | 8/2002 | Hewson et al. | |
| 6,441,347 B1 | 8/2002 | Wu | |
| 6,554,260 B1 | 4/2003 | Lipscombe et al. | |
| 7,111,624 B2 | 9/2006 | Thudor et al. | |
| 7,364,140 B2 | 4/2008 | Lipscombe et al. | |
| 7,712,249 B1 | 5/2010 | Modlin et al. | |
| 8,253,076 B2 | 8/2012 | Andel et al. | |
| 9,174,017 B2 * | 11/2015 | Potharaju | A61M 16/109 |
| 10,252,019 B2 * | 4/2019 | Potharaju | A61M 16/16 |
| 2003/0040722 A1 | 2/2003 | Massengale et al. | |
| 2003/0198802 A1 | 10/2003 | Vinod | |
| 2005/0260027 A1 | 11/2005 | Levy | |
| 2008/0149512 A1 | 6/2008 | Dane | |
| 2008/0206506 A1 | 8/2008 | Vinod | |
| 2009/0000620 A1 | 1/2009 | Virr | |
| 2009/0107980 A1 * | 4/2009 | Andel | A61M 16/024 219/443.1 |
| 2009/0107981 A1 | 4/2009 | Andel et al. | |
| 2010/0130085 A1 | 5/2010 | Yu | |
| 2010/0168326 A1 | 7/2010 | Scholz et al. | |

FOREIGN PATENT DOCUMENTS

| | | |
|---|---|---|
| WO | WO 2007/019625 A1 | 2/2007 |
| WO | WO 2008/027670 A1 | 3/2008 |
| WO | WO 2008/056993 | 5/2008 |

OTHER PUBLICATIONS

Extended Search Report in corresponding European Patent Application No. 19211737.2, dated May 12, 2020, in 6 pages.
International Search Report; PCT/NZ2010/000103; 3 pages.
Supplemental European Search Report; dated May 23, 2014; 7 pages.
Office Action in corresponding Canadian Patent Application No. 2,764,382, dated Feb. 2, 2016, in 3 pages.
Examination Report in corresponding European Patent Application No. 16205443.1, dated Sep. 18, 2018, in 5 pages.

* cited by examiner

SECTION D-D

SECTION D-D

HUMIDIFIER HEATER BASE

CROSS-REFERENCE TO RELATED APPLICATIONS

This application is a continuation of U.S. patent application Ser. No. 14/838,168, filed Aug. 27, 2015, which is a continuation of U.S. patent application Ser. No. 13/375,975, filed Jan. 4, 2012, now U.S. Pat. No. 9,176,017, issued on Nov. 3, 2015, which is a national phase of International Application No. PCT/NZ2010/000103, filed Jun. 3, 2010, which claims priority from U.S. Provisional No. 61/184,379, filed Jun. 5, 2009.

BACKGROUND OF THE INVENTION

Field of the Invention

This invention relates to a gas humidification apparatus, particularly but not solely for humidifying a gases supply to a patient or user who require a supply of humidified gas for the treatment of diseases such as Obstructive Sleep Apnea (OSA), snoring, or Chronic Obstructive Pulmonary Disease (COPD) and the like. In particular, this invention relates to the heater base arrangement of a humidification apparatus.

Description of the Related Art

Devices or systems for providing a humidified gases flow to a patient for therapeutic purposes are well known in the art. Systems for providing therapy of this type, for example CPAP therapy, have a structure where gases at the required pressure are delivered from an assisted breathing unit or blower unit to a humidifier chamber downstream from the blower. As the gases are passed through the heated, humidified air in the humidifier chamber, they become saturated with water vapour. The gases are then delivered to a user or patient downstream from the humidifier, via a gases conduit. Humidified gases can be delivered from a modular system that has been assembled from separate units (that is, a system where the humidifier chamber/heater and the breathing unit/blower are separate items) connected in series via conduits. However, it is becoming more common for integrated blower/humidifier systems to be used, as shown schematically in FIG. 1. A typical integrated system consists of a main 'blower' or assisted breathing unit which provides a pressurised gases flow, and a humidifier unit that mates with or is otherwise rigidly connected to the blower unit. This mating occurs for example by a slide on or push connection, so that the humidifier is held firmly in place on the main blower unit. An example of a system of this type is the Fisher and Paykel Healthcare 'slide-on' water chamber system shown and described in U.S. Pat. No. 7,111,624.

Integrated devices are generally more compact and discrete than modular breathing circuit that have been assembled from separate units. A compact and discrete unit is particularly advantageous for home use units, where bedside space is limited, and where a user may also have to transport and set up their own personal unit elsewhere, for example if staying overnight away from home. With compact and integrated units, the set up is generally easier for a user.

Generally, home units are used for the relief of sleep apnoea. A mid-use point will usually be during the night, during a users sleep cycle. If refilling or similar is required during use, a user will need to wake up to perform this operation. Having been woken up, the user is required to refill the humidifier chamber. Problems can arise when filling or cleaning these units, as nearly all of the respiratory humidification systems currently available use water as a humidification medium, and cleaning will almost always be carried out with a water based cleaner. Blower and humidifier units are operated and controlled electrically, and problems can occur if the internal electronic parts are not protected. If the internal parts are not protected, any accidental water spillage that takes place can potentially short-circuit the electronics and disrupt the operation of the system.

It is an object of the present invention to provide a breathing assistance apparatus which goes some way to overcoming the abovementioned disadvantages or which at least provides the public or industry with a useful choice.

SUMMARY OF THE INVENTION

In a first aspect, the present invention broadly consists in a heater base assembly for use in a humidifier of the type which is used for heating and humidifying a flow of respiratory gases supplied to a user, comprising: a heater plate having a thermally conductive portion and a perimeter portion around the perimeter of said heater plate, a resilient member having a first portion coupled to said heater plate and a second portion adapted to provide a flange around at least part of said perimeter portion, said resilient member adapted to allow said heater base to be fixed to said humidifier by said flange in such a manner that said heater plate and said first portion can move relative to said humidifier.

In a second aspect the present invention broadly consists in a heater base assembly for use in a humidifier of the type which is used for heating and humidifying a flow of respiratory gases supplied to a user, comprising: a heater plate and a resilient member fixed to the heater plate for resiliently mounting the heater plate to the humidifier and providing a fluid barrier between the heater plate and the humidifier.

Preferably the resilient member is a flexible gasket or diaphragm for resiliently fixing the heater plate to said humidifier.

Preferably said resilient member is moulded to said heater plate.

Preferably the first portion is attached to the perimeter portion of the heater plate.

Preferably the flange extends around the full perimeter of the heater plate.

Preferably the resilient member is adapted to allow said heater base to be fixed to said humidifier by said flange in such a manner that said heater plate and said first portion can move relative to said humidifier in a direction substantially transverse to the general plane of said heater plate.

Preferably said thermally conductive portion of said heater plate is substantially planar, and at least part of said perimeter portion is formed out of plane from said thermally conductive portion.

Preferably said thermally conductive portion of said heater plate has an upper surface adapted for supporting a humidifier chamber in use, and said perimeter portion is formed so that in use at least part of said perimeter portion is below said upper surface.

Preferably the flange is adapted to be clamped between two humidifier components to secure the heater base to the humidifier, at least a portion of the flange being adapted to be at least slightly compressed between the two humidifier components.

Preferably the flange is adapted to be clamped between an upper humidifier component and a lower humidifier component, at least a portion of the flange being adapted to be at least slightly compressed between the upper humidifier component and the lower humidifier component.

Preferably said resilient member has an upper circumferential groove formed in the upper surface of said flange for accepting a corresponding circumferential projection extending downwards from an upper humidifier component.

Preferably said resilient member has a lower circumferential groove formed in the lower surface of said flange for accepting a corresponding circumferential projection extending upwards from a lower humidifier component.

Preferably said upper and lower circumferential grooves are vertically aligned.

Preferably a portion of the flange is adapted to in use provide a fluid barrier between the heater base and a humidifier component.

Preferably a portion of the flange is adapted to in use provide a fluid barrier between the heater base and a humidifier component, the fluid barrier being located between the upper groove and a lower humidifier component.

Preferably a portion of the flange is adapted to in use provide a fluid barrier between the heater base and a humidifier component, the fluid barrier being located between the lower groove and an upper humidifier component.

Preferably in use a portion of said flange is elastically compressed by substantially between 4% and 20%.

Preferably in use a portion of said flange is elastically compressed by substantially 12%.

Preferably at least one and preferably both of said upper and lower circumferential grooves taper from a wide mouth to a narrow base.

Preferably said resilient member comprises a narrow section formed in said resilient member between said first portion and said flange, said narrow section providing an area in which said resilient member preferentially elastically deflects when said heater plate is displaced relative to said flange of said resilient member in a direction substantially transverse to said general plane of said heater plate in use.

Preferably said narrow section comprises a circumferential valley formed in either an upper surface or a lower surface of said resilient member or both.

Preferably said resilient member comprises a skirt section formed in said resilient member between said first portion and said flange, in use said skirt section elastically deflecting when said heater plate is displaced relative to said flange of said resilient member in a direction substantially transverse to said general plane of said heater plate.

Preferably the first portion is vertically spaced from the flange by the skirt section.

Preferably said resilient member is formed as a continuous layer across the upper surface of said heater plate, said continuous layer completely covering said upper surface.

Preferably said heater base further has a heating element attached to the underside of said heater plate.

Preferably said heater base further has at least one electrical component coupled to the underside of said heater plate, and said resilient member further has a channel formed in the lower surface of said resilient member and running from an inner part or surface of said resilient member to an outer part or surface of said resilient member, said electrical component further having electrical wires that in use extend from said electrical component across said resilient member via said channel.

Preferably in use the resilient member forms a fluid barrier between the heater plate and the humidifier.

In a third aspect the present invention broadly consists in a humidifier of the type which is used for heating and humidifying a flow of respiratory gases supplied to a user, said humidifier adapted to heat the contents of a humidifier chamber which is removably attached in use to said humidifier, said humidifier comprising: a casing or base unit, adapted to hold said humidifier chamber in position relative to said humidifier, a heater base fixed to said casing or base unit, comprising a heater plate and a resilient member, a heating element, said heater plate having a thermally conductive portion and a perimeter portion around the outside of said thermally conductive portion, said resilient member having a first portion coupled to the heater plate, and second portion providing a flange around at least part of said perimeter portion, said heater base fixed to said casing or base unit by said flange in such a manner that said heater plate and said first portion can move relative to said casing or base unit, said heating element adapted to provide heat to said thermally conductive portion of said heater plate in use.

In a forth aspect the present invention broadly consists in a humidifier of the type which is used for heating and humidifying a flow of respiratory gases supplied to a user, said humidifier adapted to heat the contents of a humidifier chamber which is removably attached in use to said humidifier, said humidifier comprising: a casing or base unit, adapted to hold said humidifier chamber in position relative to said humidifier, a heater base fixed to said casing or base unit, comprising a heater plate and a resilient member fixed to the heater plate for resiliently mounting the heater plate to the casing or base unit and providing a fluid barrier between the heater plate and the casing or base unit, and a heating element for providing heat to the heater plate.

Preferably the resilient member is a flexible gasket or diaphragm for resiliently fixing the heater plate to the humidifier.

Preferably said resilient member is moulded to said heater plate.

Preferably the first portion is attached to the perimeter portion of the heater plate.

Preferably the flange extends around the full perimeter of the heater plate.

Preferably the resilient member is fixed to said casing or base unit by said flange in such a manner that said heater plate and said first portion can move relative to said humidifier in a direction substantially transverse to the general plane of said heater plate.

Preferably said thermally conductive portion of said heater plate is substantially planar, and said perimeter portion is formed out of plane from said thermally conductive portion.

Preferably said thermally conductive portion of said heater plate has an upper surface adapted for supporting a humidifier chamber in use, and said perimeter portion is formed so that in use at least a part of said perimeter portion is below said upper surface.

Preferably the casing or base unit further comprises two humidifier components and the flange is clamped between said two humidifier components to secure the heater base to said casing or base unit, at least a portion of the flange being at least slightly compressed between the two humidifier components.

Preferably the casing or base unit further comprises an upper humidifier component and a lower humidifier component and the flange is clamped between said upper humidifier component and said lower humidifier component, at least a portion of the flange being at least slightly compressed between the upper humidifier component and the lower humidifier component.

Preferably said resilient member has an upper circumferential groove formed in the upper surface of said flange, and said upper humidifier component has a corresponding circumferential projection extending downwards from said upper humidifier component and into said upper circumferential groove.

Preferably said resilient member has a lower circumferential groove formed in the lower surface of said flange, and said lower humidifier component has a corresponding circumferential projection extending upwards from said lower humidifier component and into said lower circumferential groove.

Preferably said upper and lower circumferential grooves and corresponding said projections are vertically aligned.

Preferably a portion of the flange provides a fluid barrier between the heater base and a said humidifier component.

Preferably a portion of the flange provides a fluid barrier between the heater base and the humidifier casing or base unit and the fluid barrier is located between the upper groove and the humidifier lower component.

Preferably a portion of the flange provides a fluid barrier between the heater base and the humidifier casing or base unit and the fluid barrier is located between the lower groove and the humidifier upper component.

Preferably in use a portion of said flange is elastically compressed by substantially between 4% and 20%.

Preferably in use a portion of said flange is elastically compressed by substantially 12%.

Preferably at least one and preferably both of said upper and lower circumferential grooves taper from a wide mouth to a narrow base, the corresponding projections being correspondingly tapered to match.

Preferably said resilient member comprises a narrow section formed in said resilient member between said first portion and said flange, said narrow section providing an area in which said resilient member preferentially elastically deflects when said heater plate is displaced relative to said flange of said resilient member in a direction substantially transverse to said general plane of said heater plate in use.

Preferably said narrow section comprises a circumferential valley formed in either an upper surface or a lower surface of said resilient member or both.

Preferably said resilient member comprises a skirt section formed in said resilient member between said first portion and said flange, in use said skirt section elastically deflecting when said heater plate is displaced relative to said flange of said resilient member in a direction substantially transverse to said general plane of said heater plate.

Preferably the first portion is vertically spaced from the flange by the skirt section.

Preferably said resilient member is formed as a continuous layer across the upper surface of said heater plate, said continuous layer completely covering said upper surface.

Preferably said heater base further has a heating element attached to the underside of said heater plate.

Preferably said heater base further has at least one electrical component coupled to the underside of said heater plate, and said resilient member further has a channel formed in the lower surface of said resilient member and running from an inner part or surface of said resilient member to an outer part or surface of said resilient member, said electrical component further having electrical wires that in use extend from said electrical component across said resilient member via said channel.

Preferably in use the resilient member forms a fluid barrier between the heater plate and the humidifier.

Preferably said upper component is the wall of a humidifier chamber compartment adapted for containing a humidifier chamber in use.

Preferably a lower portion of said wall of said humidifier chamber compartment includes a horizontal wall section, said flange being clamped between said horizontal wall section and said humidifier lower component.

Preferably said heater base forms at least part of a base of said humidifier chamber compartment.

Preferably said horizontal wall section and said heater base form a base of said humidifier chamber compartment.

Preferably an upper surface of the flange is off set downwardly relative to the upper surface of the first portion of the resilient member attached to the plate, so that an upper surface of the compartment wall horizontal section is approximately in plane with said upper surface of the first portion.

Preferably said humidifier comprises a locking mechanism for retaining said humidifier chamber in an installed position with the base of said humidifier chamber adjacent to and contacting said heater plate, and when in said installed position said base of said humidifier chamber displaces said heater plate downwards, said resilient member biasing said heater plate upwards against said base of said humidifier chamber.

Preferably said locking mechanism is movable from an unlocked position to a locked position and back again, in use movement from said unlocked to said locked position presses said humidifier chamber downwards against said heater plate by a distance, thereby displacing the heater plate downwards by said distance.

Preferably said heater base is assembled to said casing or base unit in such a manner that there is a gap below a bottom surface of said resilient member or heater plate or both, said gap sized to allow said heater plate to displace downwardly from a neutral position in use, the gap being greater than said distance.

Preferably said heater element is attached to an underside of said heater plate.

Preferably said heater element contacts an underside of the heater plate when said heater plate is displaced downwards to at least said installed position, said heater element out of contact with said heater plate when said heater plate is in a raised uninstalled position.

The term "comprising" as used in this specification and claims means "consisting at least in part of". When interpreting each statement in this specification and claims that includes the term "comprising", features other than that or those prefaced by the term may also be present. Related terms such as "comprise" and "comprises" are to be interpreted in the same manner.

To those skilled in the art to which the invention relates, many changes in construction and widely differing embodiments and applications of the invention will suggest themselves without departing from the scope of the invention as defined in the appended claims. The disclosures and the descriptions herein are purely illustrative and are not intended to be in any sense limiting.

The invention consists in the foregoing and also envisages constructions of which the following gives examples only.

BRIEF DESCRIPTION OF THE DRAWINGS

Preferred embodiments of the invention will be described by way of example only and with reference to the following drawings.

FIG. 7b shows a cross sectional view along the line A-A of the humidifier chamber, humidifier chamber lid and locking handle of FIG. 7a.

FIG. 9b shows a close-up of one side of the heater base assembly shown in FIG. 9a.

FIG. 10a shows a cross section of an integrated unit that incorporates the heater base assembly of FIG. 9a.

DETAILED DESCRIPTION OF THE PREFERRED EMBODIMENT

Figure 1:
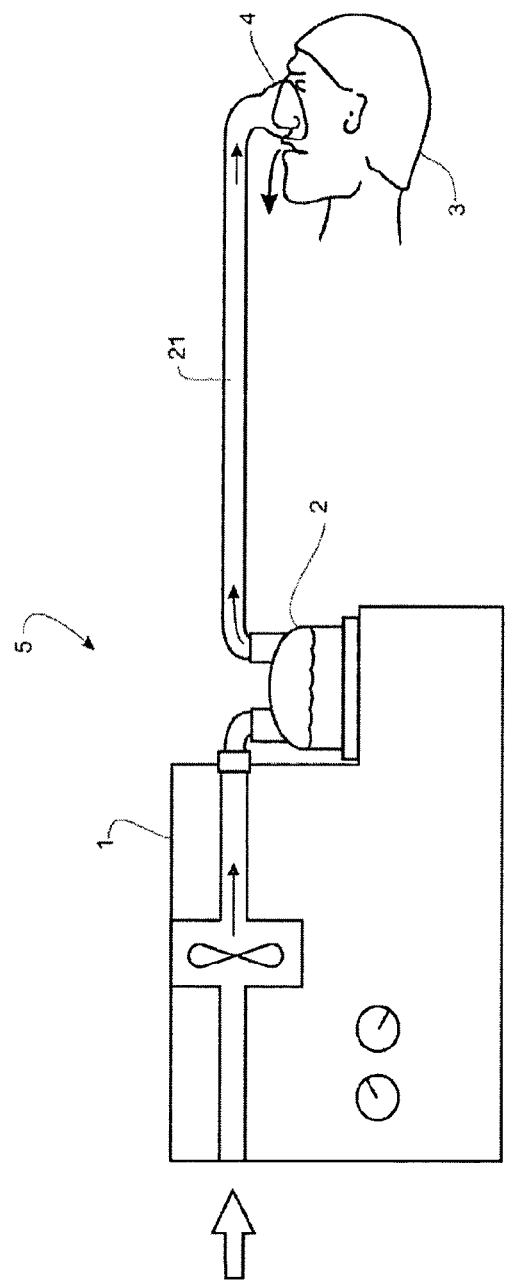
FIG. 1 shows a schematic view of a user receiving humidified air from an integrated blower/humidifier system of a known, prior art, type.

A schematic view of the user 3 receiving air from a known, prior art integrated blower/humidifier unit 5 is shown in FIG. 1. Pressurised air is provided from an assisted breathing unit or blower 1 to a humidifier chamber 2. Humidified, heated and pressurised gases exit the humidifier chamber 2 via a conduit 21, and are provided to the patient or user 3 via a user interface 4. The user interface 4 shown in FIG. 1 is a nasal mask, covering the nose of the user 3. However, it should be noted that in systems of these types, a full face mask, nasal cannula, tracheostomy fitting, or any other suitable user interface could be substituted for the nasal mask shown.

The integrated blower/humidifier unit 6 of the present invention can be substituted for the unit 5 of FIG. 1. A preferred form of the integrated blower/humidifier unit 6 is shown assembled and ready for use in FIG. 2. The integrated blower/humidifier unit 6 has two main parts: A blower unit 7, having an outer shell 36 which forms part of the blower unit 7 and also encloses the working parts of the blower unit—e.g. the fan, internal ducting and the internal control system; and a humidification unit 31 (described in detail below).

Assisted Breathing Unit

The preferred form of assisted breathing unit or integrated blower/humidifier unit 6 will now be described with reference to FIGS. 3-6.

Figure 3:
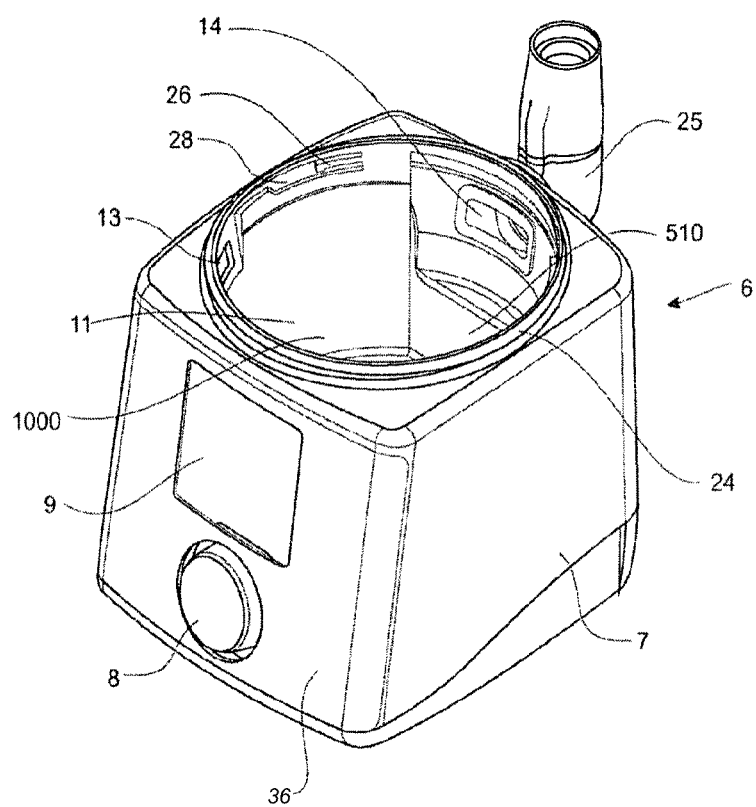
FIG. 3 shows a perspective view of the blower unit of FIG. 2, with the humidifier chamber removed (not shown).
Figure 4B:
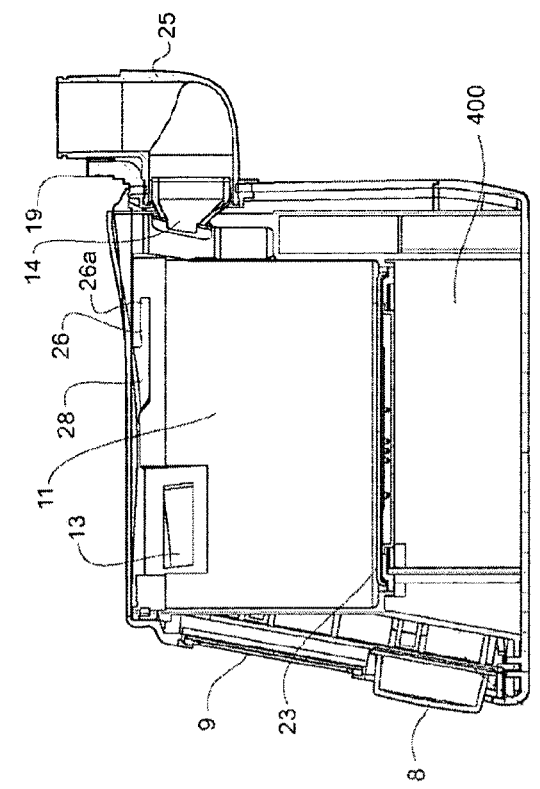
FIG. 4b shows a cross-sectional view along section line D-D of the blower unit of FIG. 2.
Figure 4A:
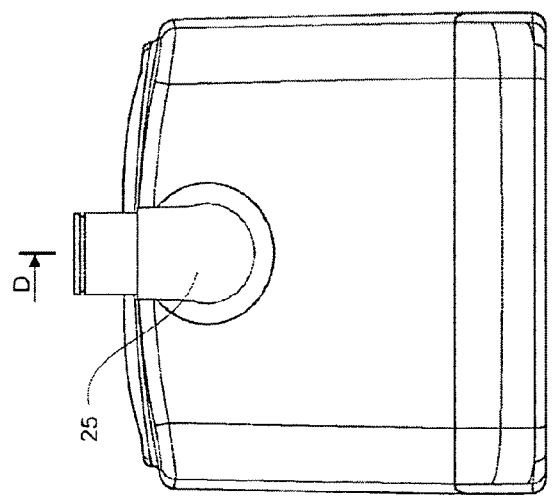
FIG. 4a shows a rear view of the blower unit of FIG. 2, with a section line D-D shown.

The integrated blower/humidifier unit 6 consists of two main parts: an assisted breathing or blower unit 7 and a humidification unit 31. The humidification unit 31 is enclosed within the external casing of the integrated blower/humidifier unit 6 in use, except for the top part. The structure of the humidification unit 31 is described in greater detail below. The blower unit 7 has an outer shell 36 which is a generally rectangular block with substantially vertical side and rear walls, and a front face that is angled slightly rearwards. In the preferred embodiment, the walls, base and top surface are all manufactured and connected as far as possible to minimise the occurrence of seams, and any necessary seams are sealed. This outer shell 36 encloses the working parts of the blower unit 7, and forms part of the blower unit 7. As shown in FIG. 3, a control knob 8 is located on the lower section of the front face of the integrated blower/humidifier unit 6, with a control display 9 located directly above the knob 8. A patient outlet 25 is shown passing out of the rear wall of the integrated blower/humidifier unit 6. In the preferred embodiment, in use the free end of the patient outlet 25 faces upwards for ease of connection. However, the preferred form of patient outlet 25 can be rotated to one side or the other to move or align it in a more convenient position for storage or for a more convenient use position. The patient outlet 25 is adapted to allow both pneumatic and electrical connection to one end of a conduit—e.g. conduit 21—running between the integrated blower/humidifier unit 6 and a patient interface—e.g. interface 4.

Figure 2:
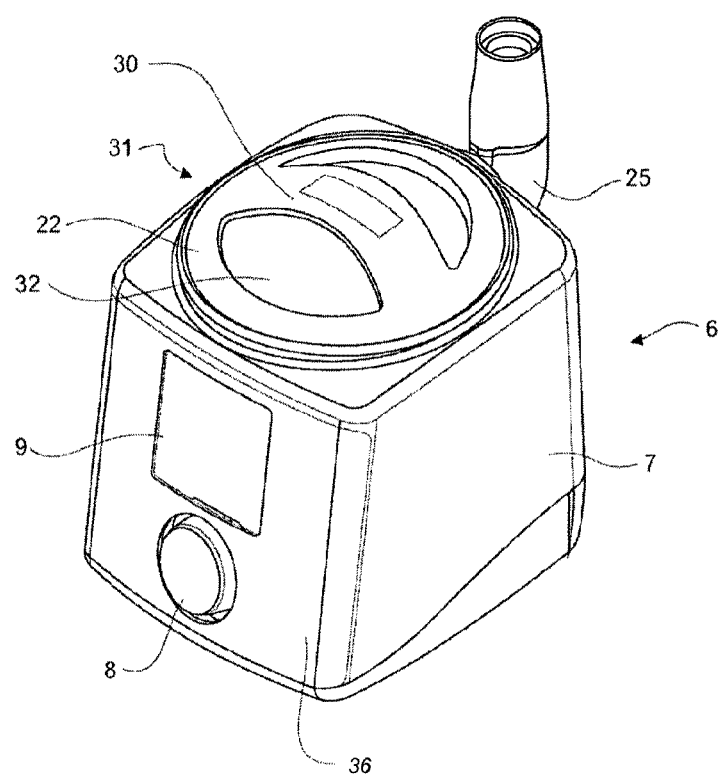
FIG. 2 shows a perspective view of the preferred embodiment of the integrated blower/humidifier (integrated unit) of one aspect of the present invention, the integrated unit having a separate humidifier chamber and blower unit which are both shown, with the humidifier chamber in place within the blower unit ready for use.

In FIG. 2, a locking handle 22 is shown in position on the top surface of the integrated blower/humidifier unit 6. The locking handle 22 is a separate item that can be unlocked and removed from the remainder of the integrated blower/humidifier unit 6. The locking handle 22 includes a grip 30, adapted to act as a handle to allow a user to lift and carry the integrated blower/humidifier unit 6, and also adapted to enable the locking handle 22 to be rotated from a locked position to an unlocked position. The locking handle 22 can be releasably locked to the remainder of the integrated blower/humidifier unit 6. The function of the locking handle 22 will be more fully described below in the 'humidifier unit' section.

FIG. 3 shows the integrated blower/humidifier unit 6 with the locking handle 22 removed and the humidification unit 31 not shown. That is, just the blower unit 7 is shown. The top surface of the blower unit 7 includes a circular humidifier aperture 1000, leading to an internal humidifier compartment 11. The opening includes a rim 24 located around the circumference of the opening. In use, a humidifier chamber 12 is located within the internal humidifier compartment 11. The humidifier chamber 12 will be described in detail below. The humidifier chamber 12 is in use fully enclosed inside the internal humidifier compartment 11, except for the uppermost part.

The internal structure of the blower unit 7 will now be described with reference to FIGS. 3 to 6. A heater base assembly 23 is located at the bottom of the internal humidifier compartment 11. The heater base assembly 23 is mounted to the floor of the internal humidifier compartment 11 in such a way that it has a small amount of elastic or compression resilience. That is, it can be pushed downwards a short distance within the compartment, but will push back against any downwards force that is applied. In the absence of any downwards force it will return to its initial position.

A blower inlet port 13 and blower outlet port 14 are located on the wall of the internal humidifier compartment 11, towards the top of the internal humidifier compartment 11. In the preferred embodiment, these blower inlet and outlet ports 13, 14 are aligned so as to mate with humidifier inlet and outlet ports 15, 16 located on the humidifier chamber 12 in use (described in detail below) so as to form a blower-to-humidifier gases route which allows gases to exit the blower unit 7 and enter the humidifier chamber 12. It should be noted that other forms of blower inlet are possible. For example a conduit running between the blower unit 7 and e.g. the lid of the humidifier chamber 12.

Figure 6:
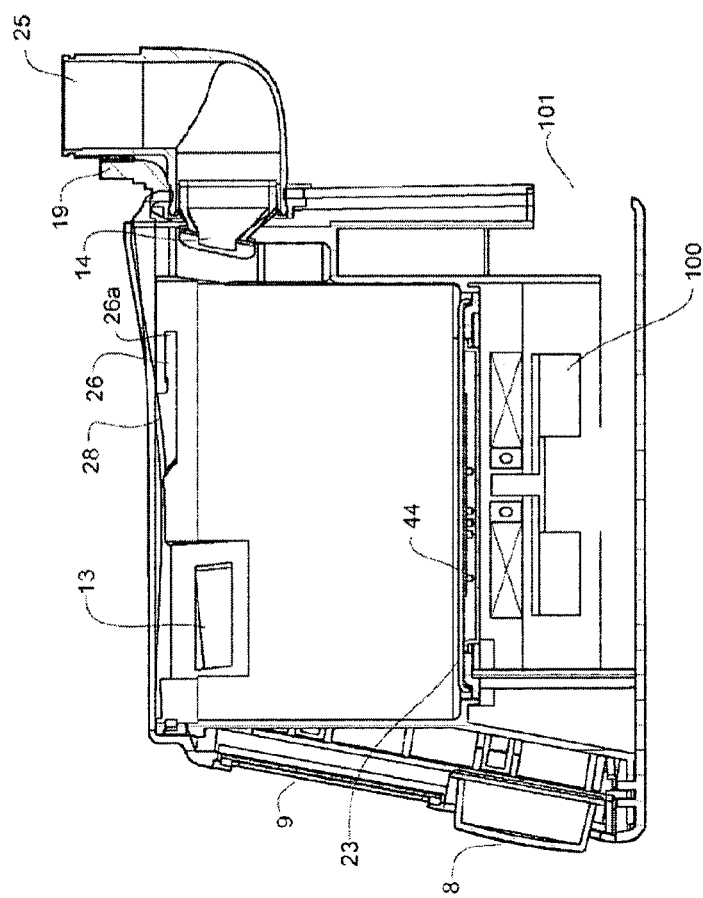
FIG. 6 shows a schematic detail view along section line DD of the internal structure of the blower unit.

As shown in FIG. 6, the integrated blower/humidifier unit 6 includes an inlet vent 101 to draw air in from atmosphere. The integrated blower/humidifier unit 6 also includes a mechanism for providing a pressurised air flow from the inlet vent 101 to the humidifier chamber. This inlet vent 101 can be located wherever is convenient on the external surface of the integrated blower/humidifier unit 6. In the preferred embodiment it is located on the rear face of the blower unit 7. In the preferred embodiment, air is drawn in through the inlet vent 101 by a blower fan unit 100 which acts as the preferred form of pressured air flow mechanism. The air is ducted or otherwise directed through the casing to the blower inlet port 13. In use, air will exit the main body of the blower unit 7 via the blower inlet port 13 and then enter the humidifier chamber 12, where it is humidified and heated, before passing out of the humidifier chamber 12 through the blower outlet port 14, which is directly connected to the patient outlet 25. The heated humidified gas is then passed to the user 3 via e.g. a conduit 21. The patient outlet 25 is adapted to enable pneumatic attachment of the conduit 21, and in the preferred embodiment, electrical connection at the patient outlet 25 is also enabled via an electrical connector 19. A combined electrical and pneumatic connection can be useful for example if the conduit 21 is to be heated. It should also be noted that the outlet connection does not have to be via the housing of the integrated blower/humidifier unit 6. If required, the connection for the conduit 21 could be located directly on an outlet from humidifier chamber 12.

The locking handle 22 and the integrated blower/humidifier unit 6 include a locking mechanism for locking the locking handle 22 to the integrated blower/humidifier unit 6. In the preferred embodiment the locking mechanism is as follows: the rim 24 includes two mating grooves 26 located just below the rim 24, spaced opposite each other on the circumference of the rim 24. More than two of the mating grooves 26 can be used if required. The grooves 26 correspond to an equal number of mating lugs 27 on the locking handle 22. The mating groove or grooves 26 have an entry point 28 on the rim 24, with the main part of the groove 26 located slightly below the rim 24. The lugs 27 are pushed downwards into the entry points 28, and the handle is rotated so that the lugs enter the main part of the grooves 26 to hold the locking handle 22 in place. Different locking mechanisms can be used if required.

Humidifier Chamber with Lid

Figure 5:
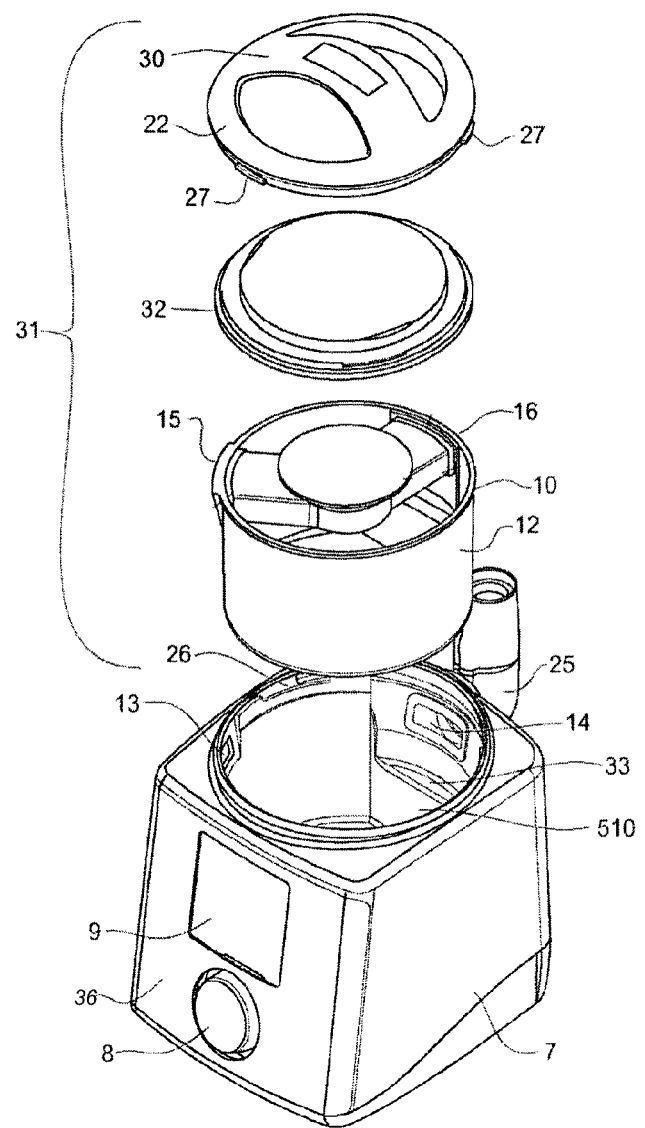
FIG. 5 shows an exploded view of the blower unit and the humidifier chamber of FIG. 2.

The humidification unit 31 will now be described in more detail with particular reference to FIGS. 5 and 7.

In the preferred embodiment, the humidification unit 31 is comprised of three main parts: humidifier chamber 12, lid 32 and locking handle 22 (counted as part of the humidifier unit for the purpose of describing the operation of the integrated blower/humidifier unit 6).

The preferred embodiment of the humidifier chamber 12 is an open-topped container, with a chamber heat conducting base 17. The humidifier chamber 12 is sized to fit snugly within the internal humidifier compartment 11 on the integrated blower/humidifier unit 6. That is, the humidifier chamber 12 is enclosed within the blower unit except for the open top of the humidifier chamber 12. A fully open topped humidifier chamber is the preferred form of the humidifier chamber 12. However, an alternative form of the humidifier chamber 12 could have a closed top surface, and would include an opening on the humidifier chamber (not necessarily on the top surface), sized appropriately so that a user can easily fill the humidifier chamber 12.

Figure 7B:
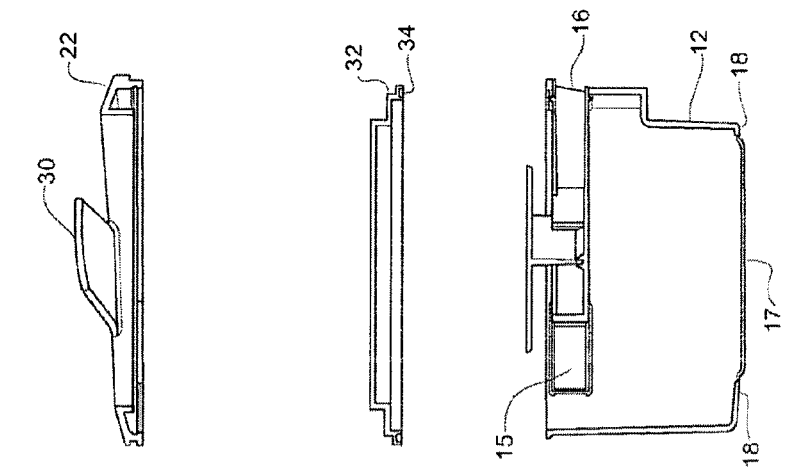
Figure 7A:
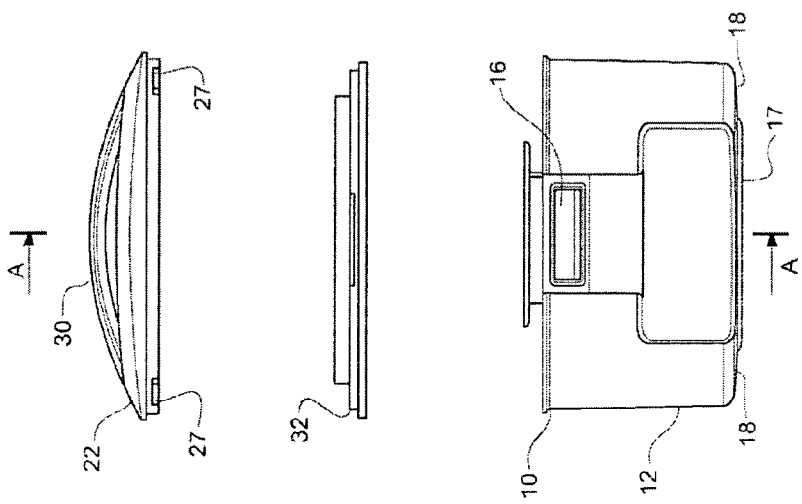
FIG. 7a shows a rear view of the humidifier chamber of the present invention, with a humidifier chamber lid and a locking handle shown in exploded view above the humidifier chamber, and a section line A-A shown.

The humidifier chamber 12 is generally circular, but the lower part of the rear (relative to the integrated blower/humidifier unit 6) is flattened as shown in FIGS. 7*a* and 7*b* to correspond to a ledge 33 on the lower rear side of the internal humidifier compartment 11. This ensures that the humidifier chamber 12 will always be oriented correctly in use. It should be understood that other methods of achieving the same result could also be used. For example, the humidifier chamber 12 and integrated blower/humidifier unit 6 could include complimentary grooves and slots. The humidifier chamber 12 can also include features such as a fill or level line if required. The humidifier inlet port 15 and a humidifier outlet port 16 are located in the wall of the humidifier chamber 12, towards the top of the chamber wall. These are positioned so as to align with the blower inlet and outlet ports 13 and 14 when the humidifier chamber 12 is in position, forming the blower-to-humidifier gases route as described above. It is preferred that the corresponding ports on the blower unit 7 and humidifier chamber 12 are shaped so as to minimise air gaps. A good seal is preferred but not required. In the preferred form, the rim or perimeter of the humidifier chamber 12 includes a chamber seal 10, formed from soft silicone or similar. When the humidifier chamber 12 is placed in position in the internal humidifier compartment 11, the chamber seal 10 is pressed against the wall or walls of the internal humidifier compartment 11, and the body of the humidifier chamber 12 and the chamber seal 10 ensure that the humidifier chamber 12 is sealed, so that air exiting the blower through the blower inlet port 13 cannot escape to atmosphere. This helps ensure that a pressurised airstream enters the humidifier chamber 12 in use. If required, a substantially unbroken ring of sealing material such as soft silicone can be added to the wall of the internal humidifier compartment 11 at or close to the upper rim of the humidifier chamber 12, to form a compartment seal (not shown) instead of or as well as the chamber seal 10. In alternative embodiments the blower inlet and outlet ports 13, 14 are surrounded by resilient sealing gaskets such as silicone gaskets to assist in forming a seal in use. If preferred, the resilient sealing gaskets around the ports can be used as well as the compartment and/or chamber seals.

In use, the humidifier chamber 12 is positioned (in the correct orientation) within the internal humidifier compartment 11. The lid 32 is then placed on top of the humidifier chamber 12. The lid 32 is sized so that it will pass through the top opening of the integrated blower/humidifier unit 6, with the lower surface of the lid 32 sealing onto the upper edge of the humidifier chamber 12. In the preferred embodiment, the lid 32 has an edge perimeter portion that is aligned facing downwards. This has a circumferential recess 34 that is filled with a silicone seal or similar which is pressed onto the upwards facing edge of the humidifier chamber 12 when the lid 32 is in position. This arrangement is shown in FIG. 7. In FIG. 7 the locking handle 22 is also shown vertically above the lid 32 (separate from the lid 32). The lid 32 is sized to fit into a recess shown in the locking handle 22 (if the handle shown in FIG. 7 is pressed vertically downwards onto the lid 32). The lid 32 is placed in position on the humidifier chamber 12 once the humidifier chamber 12 has been filled. The locking handle 22 is then positioned above the lid 32. As has been described above, lugs 27 on the circumference of the locking handle 22 engage with complimentary grooves of grooves 26 on the rim 24.

The compartment and chamber with lid are sized so that the chamber heat conducting base 17 is in contact with at least the plate 44 of the heater base assembly 23 as an upper surface of the lugs 27 contact an upper side of corresponding grooves of grooves 26. The upper side of grooves 26 is ramped downwards, from the entry point 28 towards the closed end 26a of the grooves. Rotation of the locking handle to slide lugs 27 into grooves 26 creates downwards movement of the humidifier chamber 12 against the heater base assembly 23. Once the lugs have reached the closed end 26a of grooves 26, the humidifier chamber 12 is in a fully installed position. In the fully installed position, the chamber heat conducting base 17 is pressed against at least the plate 44 of heater base assembly 23.

In normal use, a user typically presses or pushes the locking handle downwards, pushing both the lid 32 and the humidifier chamber 12 downwards onto the plate 44 of the heater base assembly 23. The heater base assembly 23 will give slightly under the downwards pressure, allowing the locking handle 22 to be rotated so that the lugs 27 engage with the grooves 26. Once the downwards force is removed, the humidifier chamber 12, lid 32, and locking handle 22 will be pressed upwards by the reaction force from the resiliently mounted heater base assembly 23, with the assembly held in place by the lugs 27 and grooves 26.

In the one embodiment shown in FIG. 3, the grooves 26 are shaped so that the locking handle 22 cannot be rotated to disengage the lugs 27 without pressing the locking handle 22 downwards slightly first.

In the preferred form, the top portion of the lid 32 fits into a central recess in the handle 22, as can best be seen in FIG. 7. The lid 32 and the locking handle 22 are sized so that the lid 32 will snap-fit and be held in place in the locking handle 22 to form an integrated lid unit. The lid 32 can be disengaged from the locking handle 22 by pressing on its top surface or similar. However, it is preferred that the snap-fit will keep them engaged in normal usage. As the handle recess and the lid 32 are circular, they can easily rotate relative to one another when engaged. When the locking handle 22 is rotated to disengage it from the integrated blower/humidifier unit 6, it will rotate easily relative to the lid 32 (which will not rotate easily due to the seal on the perimeter edge). When the locking handle 22 has been disengaged from the integrated blower/humidifier unit 6, it can be lifted away from the integrated blower/humidifier unit 6 to remove both the locking handle 22 and the lid 32.

Heater Base Assembly

The heater base assembly 23 has been described above as part of a combined blower/humidifier unit for the purpose of describing the operation of the integrated blower/humidifier unit 6. However, the heater base assembly 23 forms part of a humidifier sub-unit, with the plate 44 of the heater base assembly 23 in use providing heat to the humidifier chamber 12 for heating the liquid and gaseous contents of the humidifier chamber 12 in order to produce water vapour for humidifying the gases flow through the humidifier chamber 12. The heater base assembly 23 described below may be incorporated into an integrated blower and humidifier unit such as the integrated blower/humidifier unit 6 described above, or the heater base assembly 23 may be incorporated into a separate humidifier unit that is used as one of several components in a modular respiratory system. Where a humidifier unit is referred to below and in the claims, it is intended for this to mean either a separate humidifier unit (modular system) or a humidifier unit that is a sub-unit forming part of an integrated unit such as integrated blower/humidifier unit 6.

Figure 8:
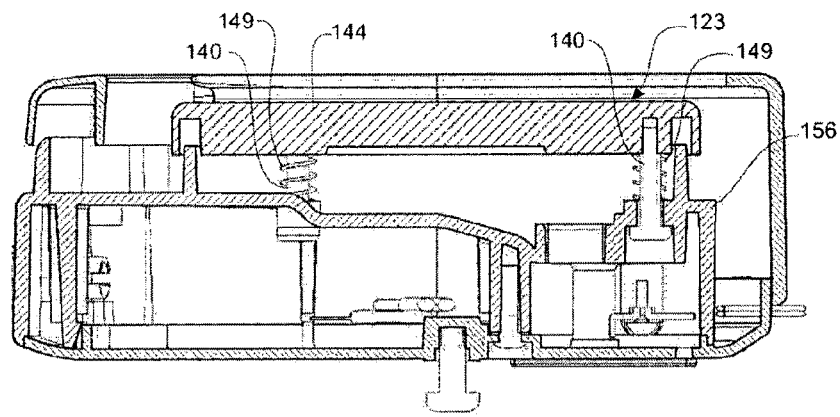
FIG. 8 shows a cross section of a prior art heater plate mounting arrangement

A heater base assembly of a typical humidifier such as those known in the art generally has a small amount of elastic or compression resilience, to in use provide a positive force against the base of a humidifier chamber. A positive force between the chamber base and the heater base ensures good thermal contact between the two. A cross section of a typical prior art heater base assembly is shown in FIG. 8. Heater plate 144 is formed from a conductive material such as aluminium, and has an upper surface which is generally planar and which acts as a heating surface in use. A heater element is attached (not shown) to provide heat to the heating surface. In use, the conductive base of a humidifier chamber contacts heater plate 144, the chamber base heated by the contact with the upper heating surface of the heater plate 144, the chamber base providing heat to the contents of the chamber. In the prior art arrangement shown, the heater plate 144 is supported by a plurality of posts 140. Posts 140 are moveably coupled to a base or base assembly 156. A resilient element or elements, in this example a plurality of helical springs 149 corresponding with support posts 140, are provided between the heater plate 144 and the base 156, to bias the plate towards the chamber (not shown) which in use is supported by the heater plate 144. In use, the chamber is pressed down onto the heater base assembly against the heater plate 144, and the force of the springs 149, and is locked in place by a locking mechanism. The springs provide a positive upwards force to bias the plate against the base of the chamber to ensure good thermal contact.

The prior art assembly of FIG. 8 does not provide any fluid barrier between the heater plate 144 and other heater base components. For example, should a user spill water from a chamber onto the heater base 123, water may flood beneath the heater plate 144. Such a spill can be inconvenient and difficult to clean and may cause damage to humidifier or integrated blower electrical components.

Figure 9A:
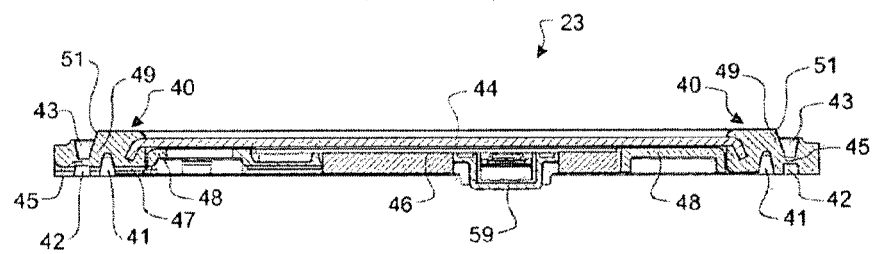
FIG. 9a shows a cross-sectional view of a preferred form of a heater base assembly.
Figure 9B:
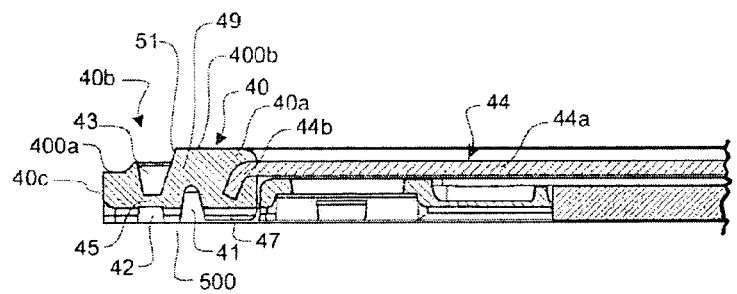
Figure 10A:
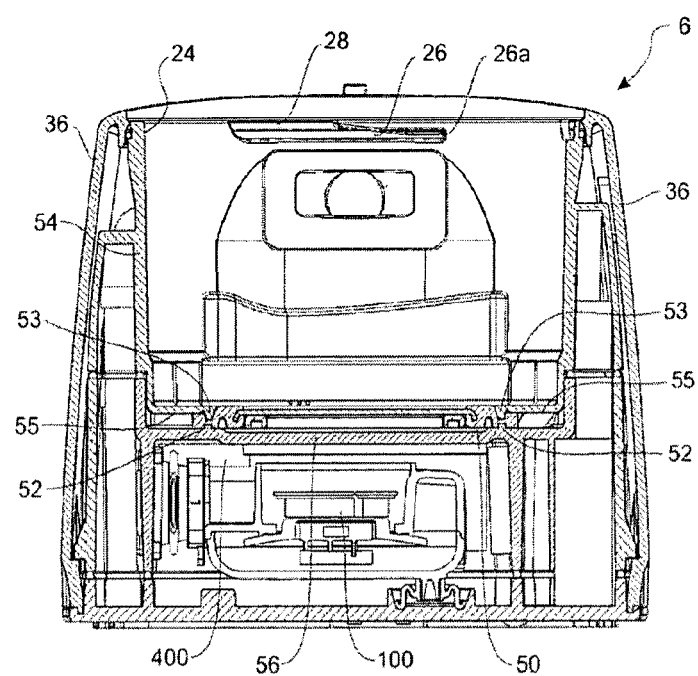

A cross section of an integrated unit that includes an embodiment of the present invention is shown in FIG. 10a. The integrated unit of FIG. 10 includes a heater base assembly 23. The heater base assembly 23 is shown separately and in greater detail in cross section in FIGS. 9a and 9b. With reference to FIG. 9a, the heater base assembly 23 comprises two main parts: a heater plate 44, and a resilient member 40 which is attached to the heater plate 44.

The heater base assembly 23 will now be described in more detail with reference to FIGS. 9a and 9b. The heater plate 44 is a generally thin flat planar item in the preferred embodiment. In the preferred embodiment, at least a portion of the heater plate is formed from a heat-conductive metal such as aluminium. The heater plate 44 has a thermally conductive portion 44a, and a perimeter portion 44b which runs around the outside of the thermally conductive portion. Preferably the thermally conductive portion 44a and the perimeter portion 44b are integrally formed. It is preferred that at least part of and preferably the majority of the perimeter portion 44b is formed out of plane with the thermally conductive portion 44a. That is, in use, the perimeter portion 44b is below the thermally conductive portion 44a. Preferably plate 44 is formed to the desired size and shape by stamping and pressing from sheet material. Alternatively heater plate 44 could be machined from a parent material. Preferably plate 44 is round. It should also be noted that although a flat planar plate has been described as the preferred embodiment above, the plate 44 could be otherwise shaped—for example concave or convex if required.

In the preferred embodiment, the resilient member 40 is attached to plate 44 by an over moulding process. In the preferred embodiment, at least the perimeter portion 44*b* of plate 44 is located within a mould cavity into which an uncured or unset resilient material is injected. Following cure or setting of this material, the resilient member 40 is formed. An inner portion 40*a* of the resilient member is attached to the perimeter portion 44*b* of plate 44.

Preferably the resilient material is silicon or other suitable resilient or rubber material known in the art.

Preferably the perimeter portion 44*b* of the plate 44 is moulded into the resilient member following the overmoulding operation described above. As outlined above, it is most preferred that the perimeter portion 44*b* is formed out of plane with the main portion or thermally conductive portion of plate 44. For example, the perimeter portion 44*b* of the plate 44 may be bent downwards during a cutting or stamping operation when forming the plate 44 from a sheet material. This provides improved mechanical strength in a direction normal to the plane of the plate 44 (this direction also being a direction in which the plate is deflected in use), and provides improved mechanical bond strength for a given size of heater base assembly 23. Preferably the out of plane portion of plate 44 is formed so that in use it is below that portion of the plate 44 which in use acts as the thermally conductive portion which is in contact with the base of the humidifier chamber. It should be noted that 'below' in this context is used to indicate that the out-of-plane portion is lower than the thermally conductive portion—'below' is not used in the sense that the out-of-plane portion has to be underneath the thermally conductive portion (i.e. 'below' is used in the sense that the out-of-plane portion is not necessarily obscured from view by the thermally conductive portion if the heater plate is viewed from directly above. However, 'below' is used in the sense that this construction (obscured from view) is not excluded, either).

Alternatively, the perimeter portion of the plate could be formed upwardly. However this is less preferred as the resilient member, being attached to the perimeter of the plate, would extend upwardly of the upper surface of the thermally conductive portion 44*a* of the plate 44. With the perimeter portion 44*b* formed downwardly according to the preferred embodiment, the resilient member can be attached to the plate so that an upper surface of the plate 44 is adjacent to or in plane with an upper surface of the resilient member 40.

In the preferred embodiment, a heating element (indicated as item 46 in FIG. 9*a*) is attached to the bottom of the plate 44. Preferably the heating element 46 is attached to the bottom of plate 44 via double sided adhesive tape. Other electrical components such as a thermal protection device may also be attached to the bottom of plate 44. Electrical wires associated with the heating element 46 and any other electrical components are routed away from the heater plate and associated components via a channel 47 (or channels) which are formed in the lower surface 500 of the resilient member 40, these channels running from the innermost part or surface of the resilient member 40 to the outermost part or surface of the resilient member 40. In the preferred form, the heater plate 44 is circular or substantially circular, and the channel or channels such as channel 47 are preferably radially aligned with respect to the plate 44.

The electrical components including the heating element 46 may be encapsulated, for example by a potting resin. A frame 48, for example a plastic frame for surrounding electrical components, may also be fixed to the bottom of the heater plate 44. If used, frame 48 provides a cavity into which a potting resin may be poured. Some electrical components, such as a thermal overload protection device, may be encased by a resilient boot 59, the resilient boot being assembled onto the plate prior to encapsulating other electrical components and wires with, for example, a potting resin.

Alternatively, one or more electrical components may be encapsulated by the resilient material which forms resilient member 40. This resilient material attached to the perimeter of the plate 44 may be continuously formed so that it passes at least partly under the plate 44 to encapsulate one or more electrical components.

Figure 10B:
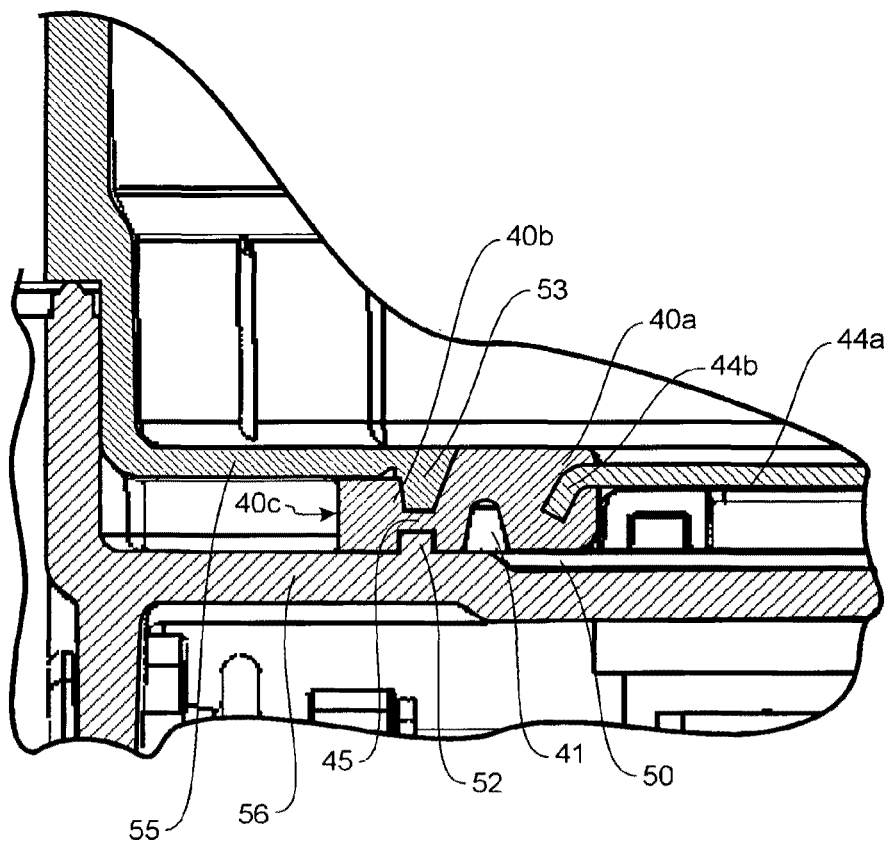
FIG. 10b shows a close up of the lower corner of the integrated unit of FIG. 10a, showing structural detail of the wall and the base of the integrated unit, and the relationship of the heater base assembly to these items.

FIGS. 10*a* and 10*b* show how the heater base assembly 23 of FIG. 9*a* may be incorporated into a humidifier assembly. In the embodiment shown, the humidifier assembly is part of an integrated blower/humidifier unit 6. However, the humidifier assembly could be part of a stand-alone humidifier. The resilient member 40 has an outer part which extends outwards from the perimeter or perimeter portion of the heater plate 44 around the perimeter or perimeter portion of the heater plate 44. As described above and as shown in FIG. 9*b*, the inner portion 40*a* of the resilient member is attached to the perimeter portion 44*b* of the heater plate 44. The outer part provides a resilient perimeter flange 40*b* around at least a part and preferably the whole of the perimeter portion of the plate. The resilient perimeter flange 40*b* is clamped in a sandwiched arrangement between two humidifier components. It is preferred that the resilient perimeter flange is clamped between an upper humidifier component and a lower humidifier component.

The open-topped internal humidifier compartment 11 is defined by a vertical compartment wall 54 extending substantially vertically from the base of the compartment. In the preferred embodiment as shown, the vertical compartment wall 54 is curved around on itself so that the internal humidifier compartment 11 is generally circular in plan view. In the preferred form shown, the flat portion 510 and ledge 33 interrupt the otherwise uniform circular nature of the internal humidifier compartment 11. These items (flat portion 510 and ledge 33) ensure correct orientation of the humidifier chamber 12 within the internal humidifier compartment 11 in use—the humidifier chamber 12 can only be positioned in the internal humidifier compartment 11 in one orientation. A lower portion of the vertical compartment wall is preferably formed as an approximately annular horizontal section 55. Horizontal section 55 forms part of the compartment base.

A humidifier compartment inner base 56 is located below the humidifier compartment base. In the preferred form, the resilient perimeter flange 40*b* of the resilient member 40 is clamped between the vertical compartment wall 54 and the compartment inner base 56. Preferably the resilient perimeter flange is clamped between the horizontal section 55 and the compartment inner base 56.

The horizontal section 55 and vertical compartment wall 54 may be integrally formed, or may be separate parts that are assembled together. Once assembled, the heater base assembly 23 and the horizontal section 55 form the base of the humidifier compartment.

Alternatively, the compartment wall may not include a lower horizontal section. In this alternative embodiment, a lower perimeter edge of the vertical wall interfaces directly with the heater base assembly 23. In this embodiment, the resilient perimeter flange is clamped between a perimeter edge of the vertical compartment wall 54 and the compartment inner base, with the heater base assembly 23 forming the base of the internal humidifier compartment 11.

The compartment inner base may form a wall of a sub housing. For example, as shown in FIG. 10a, the compartment inner base 56 is a top wall of a fan sub housing 400. The fan sub housing houses the blower fan unit 100.

The compartment inner base 56 may not extend across the full surface of the compartment base. For example, the compartment inner base 56 may be formed as an annular flange. For example, an annular flange may be attached to the compartment wall section with fasteners extending through holes passing through the resilient member 40, the resilient member 40 being clamped between the annular flange and the horizontal section 55.

The vertical compartment wall 54 and the horizontal section 55 are fixedly coupled or attached to the compartment inner base by any suitable attachment method known in the art. For example, the vertical compartment wall 54 and horizontal section 55 may be attached to the compartment inner base by screw fasteners. Alternatively the compartment wall may be clipped to the compartment inner base, the vertical compartment wall 54 p.m. a the horizontal section 55 and the compartment inner base 56 sharing mating halves of a clipping arrangement. Alternatively, the vertical compartment wall 54 and the horizontal section 55 may be attached to the outer shell 36 or other component, the compartment inner base also being attached to the outer shell 36 or same other component, fixedly coupling the vertical compartment wall 54 the horizontal section 55 and the compartment inner base 56 together.

The compartment wall and the compartment inner base 56 are formed and then assembled within the humidifier unit so that there is a fixed vertical distance between, for example, horizontal section 55 and compartment inner base 56. The wall and base items are in the preferred embodiment formed from a rigid plastic or similar so when the humidifier unit is assembled there will always be a known, fixed distance between these items or e.g. the edges and walls thereof. The fixed vertical distance between the vertical compartment wall 54 the horizontal section 55 and the compartment inner base 56, at least a portion of the resilient perimeter flange 40b is compressed slightly. Compression of the resilient member 40 assists with maintaining the position of the heater base assembly 23 within the humidifier unit assembly.

The resilient member provides a water or fluid barrier between the outside or user accessible surfaces of the humidifier and internal components of the humidifier. Compression of the resilient perimeter flange 40b between the vertical compartment wall 54 the horizontal section 55 and the compartment inner base 56 creates a fluid or water barrier between the heater base assembly 23 and the vertical compartment wall 54 and the horizontal section 55. A compressed portion of the resilient perimeter flange 40b provides a fluid barrier between the heater base assembly 23 and the upper humidifier component. The compressed portion of the resilient perimeter flange 40b provides a fluid barrier between the heater base assembly 23 and the humidifier compartment wall. In the assembled humidifier unit, the heater base assembly 23 forms at least a part of the base of the internal humidifier compartment 11. A fluid or water barrier between the heater base assembly 23 and the compartment wall ensures that at least some liquid spilt inside the humidifier compartment cannot reach the internal components of the humidifier unit. Liquid spills are preferably contained within the internal humidifier compartment 11.

Preferably the water barrier provided by the resilient member 40 is a seal that provides a water tight barrier between the heater base assembly and the mating humidifier components such as the humidifier compartment wall. Alternatively, the water barrier may provide a partial seal between the heater base assembly and the humidifier; even a partially water tight barrier that prevents some spilt fluid from passing from the humidifier compartment to the internal components of the humidifier unit can provide a useful benefit.

Preferably an upward surface 400a of the resilient perimeter flange is offset downwardly relative to the upper surface 400b of the inner portion 40a of the resilient member attached to the plate 44, so that, when assembled together, an upper surface of the compartment wall horizontal section is approximately in plane with the upper surface 400b of the resilient member 40 attached to plate 44.

As shown in FIGS. 9a and 9b, the fluid barrier portion 45 in the preferred embodiment of resilient member 40 is formed as follows: an upper groove 43 is formed in an upper surface of the resilient member. The compartment wall horizontal section has a corresponding upper projection 53 extending downwards, which locates into the upper groove 43 when the humidifier unit is assembled. Preferably the upper groove 43 extends continuously around the resilient member, the upper groove 43 being located intermediate between an outer perimeter 40c of the resilient member and an outer perimeter of the plate 44. Preferably the upper projection 53 extends continuously around an inner perimeter portion of the horizontal section 55, as shown in FIGS. 10a and 10b. Alternatively, the upper projection 53 may extend continuously around the compartment wall horizontal section at a position intermediate between an inside perimeter of the horizontal section 55 and the vertical compartment wall 54.

Preferably the upper projection 53 is tapered to assist with alignment of the compartment wall with the heater base assembly 23 during assembly of the humidifier unit. Preferably the upper groove 43 is correspondingly tapered, tapering from a wide mouth to a narrow base.

The upper projection 53 provides a reduced cross sectional area for easier compression of the resilient member 40, when compared to no projection. This allows for easier assembly of the humidifier unit as a reduced force is required to compress the resilient member to a desired state of compression. Compression of the resilient member 40 between the upper projection 53 and the compartment inner base creates the fluid barrier for containing fluid spills within the internal humidifier compartment 11.

In the most preferred form, the fluid barrier portion 45 in the resilient member 40 is further formed by the inclusion of a second groove 42 formed in the lower surface 500 of the resilient member 40. In the preferred form, the compartment inner base also has a corresponding lower projection 52 which in use extends upwards and locates within the second groove 42 when the humidifier unit is assembled. Preferably the second groove 42 extends continuously around the resilient perimeter flange 40b, the second groove 42 being located intermediate between the outer perimeter 40c of the resilient member and the outer perimeter of the plate 44. In the preferred embodiment, the lower projection 52 extends continuously around the compartment inner base 56 and corresponds to the continuous second groove 42.

In the preferred embodiment, the lower projection 52 is tapered to assist with alignment of the heater base assembly 23 onto the compartment inner base during assembly of the humidifier unit. In the most preferred form, the second groove 42 is tapered from a wide mouth to a narrow base.

The lower projection 52 provides a reduced cross sectional area for easier compression of the resilient member 40. This allows for easier assembly of the humidifier unit as a reduced force is required to compress the resilient member to a desired compression. Compression of the resilient member between the lower projection 52 and the compartment horizontal section assists in forming a fluid barrier which contains fluid spills within the internal humidifier compartment 11.

As outlined above, in the preferred form, the heater base assembly 23 has the upper groove 43 and second groove 42. Preferably the second and upper grooves 42, 43 are aligned in a vertical direction—that is, when assembled into the humidifier unit and in use, the upper groove 43 is directly above the second groove 42. The part of the resilient member 40 that is sandwiched between the vertically aligned lower and upper projections 52, 53 acts as the fluid barrier for containing spills within the internal humidifier compartment 11. Preferably the dimensions of the projections, the set distance between the projections, and the corresponding thickness of resilient material located between the second and upper grooves 42, 43 are calculated so that a vertical compression of the resilient member of approximately 12% is achieved when the humidifier unit is assembled. However, any range of compression between 4% and 20% has been found to be acceptable. A wider range could also be considered, although this is not preferred.

The resilient material either side of the fluid barrier portion 45 may be slightly compressed. Alternatively, the resilient material either side of the fluid barrier portion 45 can remain uncompressed in the assembled humidifier unit. It is most preferred that the resilient material outside of the fluid barrier portion 45 (e.g. the material between the outer perimeter 40c and the seal portion 45) is compressed slightly in the assembled humidifier unit. This compression of the resilient material outside of the fluid barrier portion 45 is less than the compression of the fluid barrier portion 45. Alternatively, the resilient material outside of the fluid barrier portion 45 can remain uncompressed in the assembled humidifier unit.

The material within the fluid barrier portion 45 (e.g. the material between the fluid barrier portion 45 and the plate 44) is compressed slightly in the assembled humidifier unit. This compression of the resilient material within the fluid barrier portion 45 is less than the compression of the fluid barrier portion 45. Alternatively, the resilient material within the fluid barrier portion 45 can remain uncompressed in the assembled humidifier unit.

As can be seen from the above description, the fluid barrier portion of the resilient member is clamped between or sandwiched between the vertically aligned lower and upper projections 52, 53. The inner portion 40a of the resilient member 40 is overmoulded and permanently connected to the heater plate 44. Therefore, the resilient member 40 provides a fluid barrier between the heater base assembly 23 and the humidifier compartment wall. Additionally the resilient member 40 acts as a suspension member as will now be described.

As shown in FIGS. 10a and 10b, in the preferred embodiment, a gap 50 is provided between the heater base assembly 23 and the compartment inner base. The gap 50 is between the lower surface 500 of the resilient member 40 and an upper surface of the compartment inner base 56. In use, the heater plate and a portion of the resilient member are displaced downwardly (with the clamped portion or resilient perimeter flange of the resilient member 40 remaining in place). Alternatively, the compartment inner base 56 may be absent except for the portion of the compartment inner base 56 clamping the resilient perimeter flange 40b.

The gap 50 allows vertical downward movement of that part of the heater base assembly 23 which is not clamped. The gap 50 is present when the resilient member 40 is un-deflected. The resilient member 40 is un-deflected when the humidifier chamber 12 is not installed within the internal humidifier compartment 11 with the plate 44 in a raised or uninstalled position. As described previously, to install the humidifier chamber 12 within the internal humidifier compartment 11, the humidifier chamber 12 is positioned within the internal humidifier compartment 11 and the lid 32 is then placed on top of humidifier chamber 12. The lid 32 and locking handle 22 is pressed down slightly, allowing the locking handle to rotate so that the lugs 27 engage with grooves 26. Pressing the lid and locking handle downwards presses the chamber heat conducting base 17 of humidifier chamber 12 onto the heater base assembly 23. The resilient member 40 of heater base assembly 23 and the gap 50 beneath the heater base assembly 23 allows the heater plate 44 to move downwards with respect to the vertical compartment wall 54 and the horizontal section 55. With the humidifier chamber 12 in the installed position, the resilient member 40 remains in a deflected state. In the deflected state, the resilient member 40 provides an upwards force, pressing or biasing the thermally conductive portion 44a of heater plate 44 against the base of e.g. humidifier chamber 12 to ensure good thermal contact.

It should be noted that the way in which the humidifier chamber 12 locks to or is held by the humidifier unit in an installed position is not important. For example, a humidifier assembly according to the present invention may not enclose the humidifier chamber within a chamber compartment as in the preferred embodiment described above. Other retaining or locking mechanisms other than the grooves 26 and lugs 27 described above may be used to retain the chamber in an installed position where the heater plate is displaced downwardly against the action of the deflected resilient member 40.

As shown in FIG. 7a or FIG. 7b, the chamber heat conducting base 17 preferably extends slightly proud of the periphery portion 18 of the base. As best shown in FIG. 9a, in the preferred embodiment, the resilient member 40 does not extend all the way across the top surface of the heater plate 44, but forms a circumferential ridge above and around the outside perimeter of the heater plate 44. The chamber heat conducting base 17 and the resilient member 40 are dimensioned so that the chamber heat conducting base 17 will fit within the saucer section formed by the ridge of resilient member 40 attached to the heater plate 44, and the chamber heat conducting base 17 directly contacts the heater plate 44 over substantially the whole of the surface of the chamber heat conducting base 17. In the preferred embodiment, the amount which the chamber heat conducting base 17 extends downwardly proud of the periphery portion 18 is slightly greater than the thickness or height of the ridge of resilient material above the surface of the heater plate 44, to ensure there is no interference between the resilient member 40 and the humidifier chamber, so that good contact between plate 44 and chamber heat conducting base 17 occurs. Alternatively the whole base of the humidifier chamber may fit within the inner dimension of the resilient member.

Preferably the gap 50 allows enough vertical movement of the heater plate 44 to allow the locking handle lugs 27 to lock fully into grooves 26 without the gap 50 completely closing. This ensures the humidifier chamber may be installed by downwards deflection of the resilient member only—that is, without further significant compression of the resilient member. This helps ensure that the force required to press the chamber into position does not become excessive. For example, in the preferred embodiment, the gap provides approximately 1.1 mm of vertical travel, and the amount of vertical travel required to slide locking lugs 27 from the entry point 28 into grooves 26 is approximately 0.7 mm.

When deflected downwards, the resilient member 40 provides an upwards force to the heater plate so that the heater plate 44 is pressed against the chamber heat conducting base 17.

The inventors have found that a force of approximately 29N is desirable for pressing the chamber onto heater plate 44 (and vice versa) to fully install the humidifier chamber 12 within the internal humidifier compartment 11. A force of this magnitude is not overly difficult for a user to over come by rotation of the locking handle lugs 27 into grooves 26, and this amount of force provides good contact pressure between the chamber heat conducting base 17 and the heater plate 44 for good thermal connection.

To achieve a desirable deflection force required to install the humidifier chamber 12 into the internal humidifier compartment 11, the resilient member further has a necked or narrow section 49 located between the inner portion 40a and the clamped portion of the resilient member 40. Narrow section 49 is formed by forming or including a valley 41 in either the lower or the upper side or surface of the resilient member 40. It is preferred that the valley 41 is formed in the bottom surface of the resilient member as shown in FIGS. 9a and 9b. Alternatively, the valley may be formed in the upper surface of the resilient member 40, or both surfaces of the resilient member.

Movement of the heater plate 44 downwards from a resting position is achieved by deflection of the resilient member 40. The clamped portion of the resilient perimeter flange 40b is clamped in position and remains stationary relative to the humidifier assembly as outlined above. The inner part or inner portion 40a is attached to the heater plate 44 and moves downwards with the heater plate 44 when the humidifier chamber is placed in position. Elastic deflection of the resilient member 40 between the inner portion 40a and the clamped portion generally occurs through the narrow section 49. The resilient member 40 deforms (generally through the narrow section 49) as it is deflected during downwards movement of the heater plate 44, and an inner side 51 of the upper groove 43 may deflect away from the upper projection 53, creating a crevice between the inner side 51 and a side of the upper projection 53. Liquid from a spill inside the compartment may enter the crevice. However, once the humidifier chamber 12 is removed from the internal humidifier compartment 11, the resilient member deflects back to a resting shape, closing the inner side 51 of the upper groove 43 against the corresponding side of the upper projection 53. This closing of the crevice squeezes liquid from the area between the upper groove 43 and upper projection 53. Due to the compression of the fluid barrier portion 45, no liquid passes beyond the fluid barrier provided by the resilient member, even with maximum deflection of resilient member 40.

In an alternative embodiment, the resilient member is formed continuously across the upper surface of the heater plate, completely covering the upper surface of the heater plate. During the over moulding process, the uncured or unset resilient material is allowed to flash across the upper surface of the heater plate 44, creating a heater base assembly with a continuous resilient material upper surface. The resilient material covering electrically isolates the heater plate from user contact, and provides corrosion protection.

In a further alternative embodiment, the heater element may be attached to the compartment inner base or other humidifier component. In this alternative embodiment, the heater element does not contact the heater plate 44 when the heater plate 44 is in a raised position with the resilient member 40 in an un-deflected state. When the humidifier chamber is installed within the humidifier compartment, the heater plate 44 is moved downwards against the action of the deflected resilient member 40 to a lowered position. In the lowered position, the bottom of the heater plate 44 makes thermal contact with the heating element attached to the inner compartment base or other humidifier component to heat the heater plate and the conductive base of the chamber above. This embodiment has the advantage that the heater plate 44 cools more quickly when the chamber is removed from the internal humidifier compartment 11, as contact between the heater plate 44 and the heater element is lost when the humidifier chamber 12 is removed from the heater plate 44. The heater element is preferably elastically mounted to the inner compartment base or other humidifier component to allow some vertical movement of the element once in contact with an underside of the heater plate. The spring constant of the elastic mounting of the heating element may be different to the spring constant of the elastic mounting of the heater plate. For example, the spring constant of the elastic mounting of the heating element could be higher than the spring constant of the elastic mounting of the heater plate.

Figure 11:
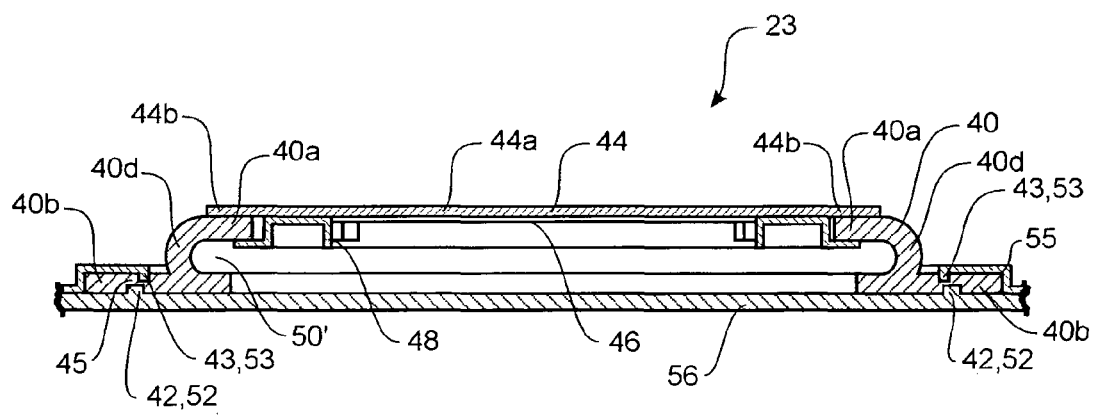
FIG. 11 shows a cross-sectional part view of an integrated unit with an alternative form of a heater base assembly.

An alternative heater base assembly is illustrated in FIG. 11. The same item numbering used to describe the previous embodiment of FIGS. 9a and 9b have been used to describe like parts of the alternative embodiment of FIG. 11.

A difference between the embodiments of FIGS. 9 and 11 is the cross sectional shape of the resilient member 40. The resilient member in the heater base assembly 23 of FIG. 11 is preferably attached to the plate 44 and assembled to a humidifier assembly as previously described with reference to the embodiment of FIGS. 9a and 9b. With reference to FIG. 11, an inner portion 40a of the resilient member 40 is attached to a perimeter portion 44b of plate 44. Preferably the resilient member is moulded to the plate. As shown in FIG. 11, the resilient member is moulded or attached to a lower surface of the plate. An outer part of the resilient member forms a resilient perimeter flange 40b around at least a part and preferably the whole of the perimeter portion of the plate. The resilient perimeter flange 40b is claimed in a sandwiched arrangement between two humidifier components, the horizontal section 55 and compartment inner base 56 in FIG. 11. A fluid barrier is formed between the heater base assembly and a humidifier compartment as previously described with reference to the embodiment of FIG. 9.

Bridging between the inner portion 40a and the resilient perimeter flange 40b of the resilient member is a skirt portion 40d. The skirt portion 40d allows vertical movement of the heater plate 44 with respect to the resilient perimeter flange of the resilient member.

In the illustrated embodiment, the skirt portion 40d spaces the inner portion 40a of the resilient member from the resilient perimeter flange 40b of the resilient member. A vertical gap 50' between the inner and outer parts of the resilient member allow vertical movement of the heater plate 44 relative to the outer part of the resilient member fixed to the humidifier assembly. The gap 50' is present when the resilient member is un-deflected, when the humidifier chamber 12 is not installed within the humidifier compartment with the plate 44 in a neutral or non-displaced position. Once the chamber is installed into the humidifier and on the heater base, the resilient member is deflected. In the deflected state, the resilient member provides an upwards force to bias the plate 44 against the base of humidifier chamber 12.

Preferably the gap 50' provides enough vertical movement to allow a chamber to be installed onto the heater base without the gap 50' fully closing, as previously described with reference to the embodiment of FIG. 9.

The amount of force required to displace the heater plate downwards may be determined by the thickness of the skirt portion 40*d* of the resilient member 40 or the length of the skirt section or both.

The resilient member provides a gasket or diaphragm between the heater plate 44 and the humidifier structure to resiliently mount the heater plate 44 within the humidifier assembly. The intermediate portion of the resilient member bridging between the clamped portion of the resilient member and the inner portion of the resilient member coupled to the plate 44 allows vertical movement of the heater plate.

Further alternative embodiments may present themselves to a person skilled in the art without departing from the present invention. For example, the resilient member may form a bellows shape or other shape designed to achieve a desired amount of resistance to displacement of the heater plate relative to the humidifier base or casing.

Furthermore, the resilient member may be alternatively attached to a component fixed to the heater plate. For example, the resilient member may be moulded or otherwise attached to the frame 48 attached to the bottom of the heater plate 44. Attachment of the frame to the heater plate couples the resilient member to the heater plate without direct bonding between the heater plate and the resilient member.

The heater base assembly according to the present invention is a vertically compact assembly. When assembled into a casing as part of a humidifier assembly, the compact nature of the heater base assembly helps to reduce the humidifier assembly or integrated unit assembly height to assist in achieving a desirable compact unit for home use. The heater base assembly according to the present invention when assembled as part of a humidifier assembly or integrated unit provides a fluid barrier that prevents or at least reduces spills contacting internal blower or humidifier components and contains spills within the humidifier compartment. The heater base assembly according to the present invention has a resilient element that in use acts to provide a desirable amount of force between the heater plate 44 and the conductive base of the humidifier chamber, to bias the heater plate against the base of the chamber. In the context of this specification, a desirable amount of force is an amount of force which can be easily overcome by a user when installing a humidification chamber into the humidifier, yet provides sufficient contact force to achieve good thermal contact between the chamber base and heater plate.

The foregoing description of the invention includes preferred forms thereof. Modifications may be made thereto without departing from the scope of the invention as claimed.

It should also be noted that when terms such as for example 'top', 'bottom', 'above', 'below', 'upper surface', 'lower surface' and 'underside' are used, these refer to the orientation of the device described or claimed when it is in use. These terms are used to describe the orientation or location of features relative to one another when the device is in use, and when these terms are used, should be read in this manner. Use of these terms is not intended to limit the device as described or claimed in any other fashion.

The following is claimed:

1. A respiratory humidifier system, the system comprising:
   a base unit;
   a heater plate, wherein the heater plate is resiliently mounted to the base unit by a heater plate mounting such that the heater plate can be displaced vertically, the heater plate mounting extending circumferentially around a periphery of the heater plate;
   a heating element; and
   a locking mechanism configured to retain a humidifier chamber in an installed position with a base of the humidifier chamber adjacent to and contacting the heater plate, wherein, when in the installed position, the base of the humidifier chamber displaces the heater plate downwards toward a bottom side of the base unit, wherein the heating element is located such that the heater plate contacts the heating element when the humidifier chamber is in the installed position, and the heater plate is separated from the heating element by a gap when the humidifier chamber is not in the installed position.

2. The system of claim 1, wherein the heating element is elastically mounted to the base unit by a heating element mounting to allow vertical movement of the heating element once in contact with the heater plate.

3. The system of claim 2, wherein the heating element is elastically mounted to an inner base of the base unit.

4. The system of claim 3, wherein the heating element mounting provides an upward force that presses or biases the heater plate against the base of the humidifier chamber when the humidifier chamber is in the installed position.

5. The system of claim 2, wherein the spring constant of the heating element mounting is different from the spring constant of the heater plate mounting.

6. The system of claim 2, wherein the spring constant of the heating element mounting is higher than the spring constant of the heater plate mounting.

7. The system of claim 1, wherein the base unit comprises a humidifier compartment configured to receive the humidifier chamber.

8. The system of claim 7, wherein the humidifier compartment is shaped to allow the humidifier chamber to be positioned in the humidifier compartment in one orientation.

9. The system of claim 1, wherein the locking mechanism is movable from an unlocked position to a locked position and from the locked position to the unlocked position such that movement from the unlocked position to the locked position presses the humidifier chamber downwards against the heater plate by a distance, thereby displacing the heater plate downwards by the distance.

10. The system of claim 1, wherein the heater plate is movable relative to the base unit in a direction substantially transverse to a general plane of the heater plate.

11. The system of claim 1, wherein the heater plate mounting is attached to a perimeter portion of the heater plate.

12. A respiratory humidifier system, the system comprising:
   a base unit;
   a heater plate, wherein the heater plate is mounted to the base unit by a heater plate mounting such that the heater plate can be displaced vertically;

a heating element elastically mounted to the base unit by a heating element mounting; and a locking mechanism configured to retain a humidifier chamber in an installed position with a base of the humidifier chamber adjacent to and contacting the heater plate, wherein, when in the installed position, the base of the humidifier chamber displaces the heater plate downwards toward a bottom side of the base unit, wherein the heating element is mounted such that the heater plate contacts the heating element when the humidifier chamber is in the installed position, and the heater plate is separated from the heating element by a gap when the humidifier chamber is not in the installed position, the heating element mounting configured to allow the heating element to be displaced vertically once in contact with the heater plate, and wherein the heating element mounting provides an upward force that presses or biases the heater plate against the base of the humidifier chamber when the humidifier chamber is in the installed position.

13. The system of claim 12, wherein the heater plate mounting comprises a resilient material.

14. The system of claim 13, wherein the spring constant of the heating element mounting is different from the spring constant of the heater plate mounting.

15. The system of claim 13, wherein the spring constant of the heating element mounting is higher than the spring constant of the heater plate mounting.

16. The system of claim 12, wherein the base unit comprises a humidifier compartment configured to receive the humidifier chamber.

17. The system of claim 16, wherein the humidifier compartment is shaped to allow the humidifier chamber to be positioned in the humidifier compartment in one orientation.

18. The system of claim 12, wherein the heating element is elastically mounted to an inner base of the base unit.

19. The system of claim 12, wherein the locking mechanism is movable from an unlocked position to a locked position and from the locked position to the unlocked position such that movement from the unlocked position to the locked position presses the humidifier chamber downwards against the heater plate by a distance, thereby displacing the heater plate downwards by the distance.

20. The system of claim 12, wherein the heater plate is movable relative to the base unit in a direction substantially transverse to a general plane of the heater plate.

* * * * *

UNITED STATES PATENT AND TRADEMARK OFFICE
CERTIFICATE OF CORRECTION

PATENT NO. : 11,273,281 B2
APPLICATION NO. : 16/248663
DATED : March 15, 2022
INVENTOR(S) : Venkata Subbarao Potharaju Page 1 of 1

It is certified that error appears in the above-identified patent and that said Letters Patent is hereby corrected as shown below:

In the Specification

At Column 1, Line 10 (approximately), delete "9,176,017," and insert --9,174,017,--.

At Column 4, Line 22, delete "forth" and insert --fourth--.

At Column 7, Line 29, delete "arrangement" and insert --arrangement.--.

At Column 15, Line 28, delete "a the" and insert --the--.

Signed and Sealed this
Twenty-sixth Day of December, 2023

Katherine Kelly Vidal
*Director of the United States Patent and Trademark Office*